United States Patent
Koulikov

(10) Patent No.: US 10,514,299 B2
(45) Date of Patent: Dec. 24, 2019

(54) MULTIPLE LASER OPTICAL FEEDBACK ASSISTED CAVITY ENHANCED ABSORPTION SPECTROSCOPY SYSTEMS AND METHODS

(71) Applicant: Li-Cor, Inc., Lincoln, NE (US)

(72) Inventor: Serguei Koulikov, Los Altos, CA (US)

(73) Assignee: LI-COR, Inc., Lincoln, NE (US)

(*) Notice: Subject to any disclaimer, the term of this patent is extended or adjusted under 35 U.S.C. 154(b) by 0 days.

(21) Appl. No.: 16/109,382

(22) Filed: Aug. 22, 2018

(65) Prior Publication Data

US 2018/0364101 A1 Dec. 20, 2018

Related U.S. Application Data

(63) Continuation of application No. PCT/US2017/021657, filed on Mar. 9, 2017.

(60) Provisional application No. 62/306,523, filed on Mar. 10, 2016.

(51) Int. Cl.
  *G01J 3/433* (2006.01)
  *G01N 21/39* (2006.01)
  *G01N 21/3504* (2014.01)
  *G01J 3/36* (2006.01)
  *G01J 3/10* (2006.01)

(52) U.S. Cl.
  CPC .......... *G01J 3/433* (2013.01); *G01J 3/36* (2013.01); *G01N 21/3504* (2013.01); *G01N 21/39* (2013.01); *G01J 3/10* (2013.01); *G01N 2201/06113* (2013.01)

(58) Field of Classification Search
  CPC ..... G01J 3/433; G01J 3/36; G01J 3/10; G01N 21/39; G01N 21/3504; G01N 2201/06113
  See application file for complete search history.

(56) References Cited

U.S. PATENT DOCUMENTS

| | | | |
|---|---|---|---|
| 7,012,696 B2 | 3/2006 | Orr et al. | |
| 7,437,000 B1 | 10/2008 | Rosenthal et al. | |
| 7,768,647 B2 | 8/2010 | Reeve et al. | |
| 8,659,758 B2 | 2/2014 | Koulikov et al. | |
| 8,982,352 B1* | 3/2015 | Hoffnagle | H01S 5/0687 250/573 |
| 9,989,729 B2* | 6/2018 | Koulikov | H01S 3/0071 |
| 2005/0254056 A1* | 11/2005 | Kachanov | G01J 3/10 356/437 |
| 2011/0317164 A1 | 12/2011 | Cole et al. | |
| 2015/0192468 A1 | 7/2015 | Pearman et al. | |
| 2016/0069795 A1* | 3/2016 | Koulikov | H01S 3/0071 356/437 |

OTHER PUBLICATIONS

Thorlabs, "Non-Polarizing Cub Beamsplitters," downloaded Aug. 22, 2018 at http://www.thorlabs.us/newgrouppage9.cfm?objectgroup_id=6208.

(Continued)

*Primary Examiner* — Sang H Nguyen
(74) *Attorney, Agent, or Firm* — Leydig, Voit & Mayer, Ltd.; Gerald T. Gray

(57) ABSTRACT

Systems and methods for detecting trace gases utilize a resonance optical cavity and one, two or more coherent light sources coupled to the cavity through one or more cavity coupling mirrors, whereby two or more optical cavities may share the same gas volume.

7 Claims, 13 Drawing Sheets

(56) References Cited

OTHER PUBLICATIONS

Thorlabs, "UV Fused Silica Broadband Plate Beamsplitters," downloaded Aug. 22, 2018 at http://www.thorlabs.us/newgrouppage9.cfm?objectgroup_id=6044.
Thorlabs, "Broadband Polarizing Beamsplitter Cubs," downloaded Aug. 22, 2018 at http://www.thorlabs.us/newgrouppage9.cfm?objectgroup_id=739.
Iridian Spectral Technologies, "CWDM Filter Tutorial," downloaded Aug. 22, 2018 at http://www.iridian-optical-filters.com/technical-resources/optical-filter-tutorial.
PCT/US2017/021657, Written Opinion of the International Searching Authority dated May 30, 2017; 12 pp.

* cited by examiner

MULTIPLE LASER OPTICAL FEEDBACK ASSISTED CAVITY ENHANCED ABSORPTION SPECTROSCOPY SYSTEMS AND METHODS

CROSS REFERENCES

The present application for patent claims priority to International Patent Application No. PCT/US17/21657 by Koulikov, entitled "Multiple Laser Optical Feedback Assisted Cavity Enhanced Absorption Spectroscopy Systems and Methods," filed Mar. 9, 2017; and to U.S. Provisional Patent Application No. 62/306,523 by Koulikov, entitled "Multiple Laser Optical Feedback Assisted Cavity Enhanced Absorption Spectroscopy Systems and Methods," filed Mar. 10, 2016; each of which is incorporated herein by reference.

BACKGROUND

The present disclosure relates to gas analysis systems and devices and more particularly to apparatus for measuring concentrations of gases.

BRIEF SUMMARY

The present disclosure provides systems and methods for detecting trace gases according to various embodiments which utilize a resonance optical cavity and one, two or more coherent light sources coupled to the cavity through one or more cavity coupling mirrors.

In certain embodiments, multiple laser optical feedback assisted cavity enhanced absorption spectroscopy gas analyzers are provided to measure concentrations of two or more gas components using two or more laser sources. Very often different gas species have analytical absorption lines spectrally separated from each other (e.g., methane lines are at 1.65 µm, while carbon dioxide lines are at 1.61 µm). A single source such as a distributed feedback (DFB) laser or other laser usually is not able to cover both spectral regions. In this particular situation two different sources (e.g., DFB lasers) are required. Aspects of the present disclosure describe how to couple laser light from two or more laser sources into a single resonance optical cavity. However, it might occur that the absorption lines for two gas components are in completely different spectral regions (e.g., methane lines are at 1.65 µm, while nitrous oxide lines are at 2.11 µm). So, it would either be almost impossible or too expensive to have cavity mirrors suitable for both spectral regions. In that case, according to the present disclosure, two optical cavities may share the same gas volume.

Certain aspects of the present disclosure extend single laser based optical feedback assisted cavity enhanced absorption spectroscopy instruments to multiple laser based instruments. Using multiple lasers with a single optical cell or with multiple optical cells sharing the same gas volume helps decrease the total cost of a multi gas instrument. This is because some expensive modules, such as the gas delivery system, gas pressure control, temperature control, and electronics can also be shared. In certain aspects, two or more laser beams are combined first, and the combined beam is further coupled to an enhanced cavity. The optical feedback locks the laser light to the cavity modes. Various ways or means to combine two laser beams include using broadband beam splitters, using dichroic beam splitters or filters, and using polarization-dependent beam splitters.

The present disclosure also provides a method of locking a resonant optical cavity to a molecular absorption line. It is known that when a laser coupled to a resonance optical cavity is scanned over the cavity modes, a gas within the cavity may absorb light at certain wavelengths emitted by the laser. The cavity can be tuned and locked to one of the absorption lines of the gas in the cavity. This method may be used with a single laser, when during a single scan of the laser, a cavity is locked to a gas absorption line. In additional aspects, two or more lasers are coupled to a single resonance cavity, and different lasers are used to measure the absorption of different gas species. The cavity may be locked to a single absorption line or to multiple absorption lines, which may be in the scanning range of one laser. Here and further, different isotopologues of the same gas are considered as different gas species. Two or more laser current scans (or laser cavity length scans, in the case of external cavity lasers) at different laser temperatures are also considered as laser scans using different lasers. One important feature of the method is an absorption line which is used for locking the cavity and is measured only in one laser scan.

Advantages of the present embodiments include an increase in the precision and accuracy of the cavity enhanced gas analyzer without using an additional wavelength meter. The present embodiments enable locking to a cavity in one spectral scan, or defining the spectral grid frequencies of the cavity modes in this scan, and using this information about cavity mode spectral grid frequencies for different laser scans.

According to an embodiment, a system for detecting two or more analyte species present in a gaseous or liquid medium is provided. The system typically includes a resonant optical cavity containing said medium and having at least two cavity mirrors, one of which is a cavity coupling mirror, the cavity having a plurality of optical resonance cavity modes, a first laser that emits continuous wave laser light, wherein the first laser is capable of being scanned whereby a mean optical frequency of the first laser is adjustable over a range of frequencies, and wherein the first laser is responsive to optical feedback light emerging from the cavity, and a second laser that emits continuous wave laser light, wherein the second laser is capable of being scanned whereby a mean optical frequency of the second laser is adjustable over a range of frequencies, and wherein the second laser is responsive to optical feedback light emerging from the cavity. The system also typically includes a beam combiner element, wherein the beam combiner element is capable of combining laser beams from the first and the second lasers, and at least one detector configured to measure an intensity of the intra-cavity optical power of light circulating in the cavity and to generate a signal representing the intra-cavity optical power of light circulating in the cavity wherein the transmissivity of at least one of the cavity mirrors is selected such that the intensities of the optical feedback light impinging on the first and second lasers are below threshold intensity values so as to ensure that frequency hold interval ranges of the optical frequency of the first and second lasers are smaller than a free spectral range of the cavity. In certain aspects, the system further includes mode matching optics configured to couple the first and second laser beams to the cavity via the cavity coupling mirror.

According to another embodiment, a system for detecting two or more analyte species present in a gaseous or liquid medium is provided. The system typically includes a resonant optical cavity containing said medium and having at least two cavity mirrors, one of which is a cavity coupling mirror, the cavity having a plurality of optical resonance cavity modes, a first laser that emits continuous wave laser light, wherein the first laser is capable of being scanned whereby a mean optical frequency of the first laser is adjustable over a range of frequencies, and wherein the first laser is responsive to optical feedback light emerging from the cavity, mode matching optics configured to couple the first laser light to the cavity via the cavity coupling mirror at an angle non perpendicular to the mirror reflective surface, a second laser that emits continuous wave laser light, wherein the second laser is capable of being scanned whereby a mean optical frequency of the second laser is adjustable over a range of frequencies, and wherein the second laser is responsive to optical feedback light emerging from the cavity, mode matching optics configured to couple the second laser light to the cavity via the cavity coupling mirror making the laser beam from the first laser impinging on the mirror and the laser beam from the second laser impinging on the mirror non-collinear, and at least one detector configured to measure an intensity of the intra-cavity optical power of light circulating in the cavity and to generate a signal representing the intra-cavity optical power of light circulating in the cavity wherein the transmissivity of at least one of the cavity mirrors is selected such that the intensities of the optical feedback light impinging on the first and second lasers are below threshold intensity values so as to ensure that frequency hold interval ranges of the optical frequency of the first and second lasers are smaller than a free spectral range of the cavity.

According to another embodiment, a system for detecting two or more analyte species present in a gaseous or liquid medium is provided. The system typically includes a resonant optical cavity containing said medium and having at least three cavity mirrors, two of which are cavity coupling mirrors, the cavity having a plurality of optical resonance cavity modes, a first laser that emits continuous wave laser light, wherein the first laser is capable of being scanned whereby a mean optical frequency of the first laser is adjustable over a range of frequencies, and wherein the first laser is responsive to optical feedback light emerging from the cavity, mode matching optics configured to couple the first laser light to the cavity via the first cavity coupling mirror at an angle non perpendicular to the mirror reflective surface, a second laser that emits continuous wave laser light, wherein the second laser is capable of being scanned whereby a mean optical frequency of the second laser is adjustable over a range of frequencies, and wherein the second laser is responsive to optical feedback light emerging from the cavity, mode matching optics configured to couple the second laser light to the cavity via the second cavity coupling mirror at an angle non perpendicular to the mirror reflective surface, and at least one detector configured to measure an intensity of the intra-cavity optical power of light circulating in the cavity and to generate a signal representing the intra-cavity optical power of light circulating in the cavity. In certain aspects, wherein the transmissivity of the first cavity coupling mirror is selected such that the intensity of the optical feedback light impinging on the first laser is below a threshold intensity value so as to ensure that a frequency hold interval range of the optical frequency of the first laser is smaller than a free spectral range of the cavity. In certain aspects, the transmissivity of the second cavity coupling mirror is selected such that the intensity of the optical feedback light impinging on the second laser is below a threshold intensity value so as to ensure that a frequency hold interval range of the optical frequency of the second laser is smaller than the free spectral range of the cavity.

According to a further embodiment, a system for detecting one or more analyte species present in a gaseous or liquid medium is provided. The system typically includes a resonant optical cavity containing said medium and having at least two cavity mirrors, one or more of which are cavity coupling mirrors, the cavity having a plurality of optical resonance cavity modes, a first laser that emits continuous wave laser light, wherein the first laser is capable of being scanned whereby a mean optical frequency of the first laser is adjustable over a first range of frequencies, mode matching optics configured to couple the first laser light to the cavity via one of the cavity coupling mirrors, a second laser that emits continuous wave laser light, wherein the second laser is capable of being scanned whereby a mean optical frequency of the second laser is adjustable over a second range of frequencies non identical to the first range of frequencies, mode matching optics configured to couple the second laser light to the cavity via one of the cavity coupling mirrors, and at least one detector configured to measure an intensity of the intra-cavity optical power of light circulating in the cavity and to generate a signal representing the intra-cavity optical power of light circulating in the cavity wherein the cavity modes are locked to one or more spectral absorption lines of the one or more analyte species presented in the first range of frequencies.

According to a further embodiment, a system for detecting two or more analyte species present in a gaseous or liquid medium is provided. The system typically includes a resonant optical cavity containing said medium and having at least two cavity mirrors, one or more of which are cavity coupling mirrors, the cavity having a plurality of optical resonance cavity modes, a first laser that emits continuous wave laser light, wherein the first laser is capable of being scanned whereby a mean optical frequency of the first laser is adjustable over a first range of frequencies, mode matching optics configured to couple the first laser light to the cavity via one of the cavity coupling mirrors, a second laser that emits continuous wave laser light, wherein the second laser is capable of being scanned whereby a mean optical frequency of the second laser is adjustable over a second range of frequencies non identical to the first range of frequencies, mode matching optics configured to couple the second laser light to the cavity via one of the cavity coupling mirrors, at least one detector configured to measure an intensity of the intra-cavity optical power of light circulating in the cavity and to generate a signal representing the intra-cavity optical power of light circulating in the cavity, and an intelligence module configured to assign frequencies for a cavity mode grid based on spectral absorption lines of the analyte species presented in the first range of frequencies.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Figure 1:
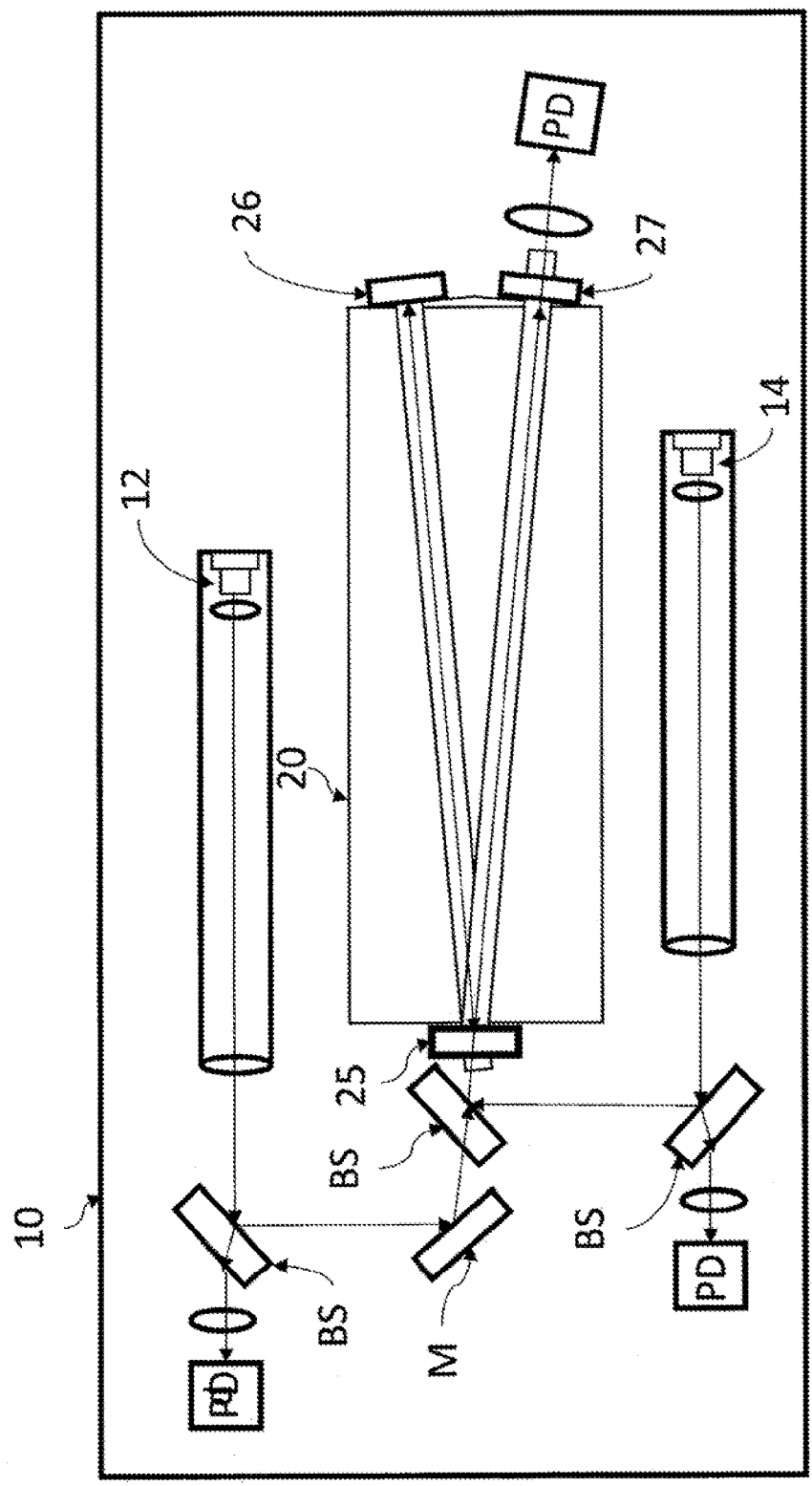
FIG. 1 shows a cavity enhanced optically spectroscopy CEOS system according to an embodiment.
Figure 1:
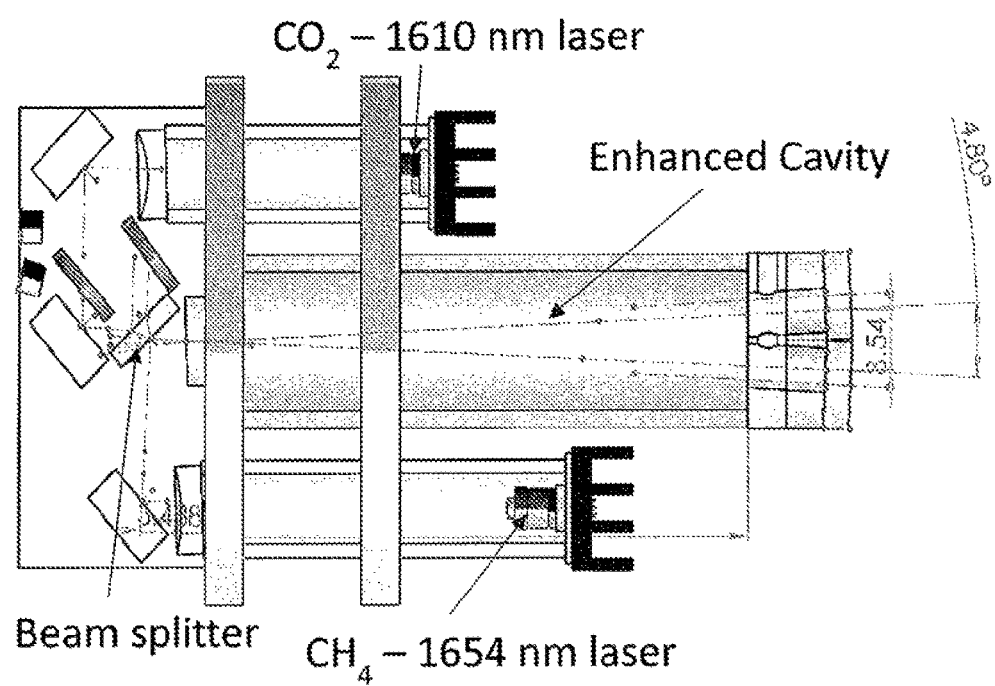

The present disclosure relates generally to trace gas detection and more specifically to resonant optical cavities and cavity enhanced absorption spectroscopy systems and methods using the same. Such systems and methods are useful for measuring components of gas mixtures, such as trace gases in air. Embodiments advantageously reduce the temperature sensitivity of the apparatus and reduce mechanical stresses caused by ambient temperature variations.

Systems and methods for detecting trace gases according to various embodiments utilize a resonance optical cavity and a coherent light source coupled to the cavity through a cavity coupling mirror. The cavity is constructed of a material having the same or a similar coefficient of thermal expansion as the mirror elements defining the cavity. For example, the main (bulk) cavity material may be the same as the main (bulk) material that forms the mirror elements, or it may be different. Such resonant cavity configurations provide improved accuracy and stability as compared to existing cavity configurations based upon similar principles.

As will be appreciated, the terms "cavity," "optical cavity," "resonant optical cavity" and the like may be used interchangeably herein.

In certain embodiments, an apparatus includes a resonant optical cavity, including high reflectivity mirrors coupled with or mounted on or to a gas-containing cell, or a housing or body structure. Typically, high reflectivity mirrors are made from glass substrates with dielectric reflective coatings on them to provide high reflectivity for specific wavelengths or wavelength ranges. One useful material used to make mirror substrates is fused silica, which has a very low thermal expansion coefficient. At the same time, gas cell bodies are typically made from metals, which may not match the thermal expansion characteristics of the mirror elements. Very often the gas cell bodies are made from stainless steel. In some applications, low thermal expansion materials such as Invar may be used.

In certain embodiments, a resonant optical cavity body structure is provided with the same materials (e.g., fused silica) used for both the high reflectivity mirrors and the gas cell body to reduce a mechanical stress in the resonant optical cavity when it is exposed to different temperatures (e.g., a temperature gradient). In certain embodiments, different materials having the same or similar thermal expansion characteristics (e.g., same or substantially similar thermal expansion coefficient) are used for the high reflectivity mirrors and the gas cell body to reduce or minimize mechanical stress due to temperature differences. Similar or substantially similar thermal expansion coefficients will have values within about $10^{-6}$ m/m K (examples include quartz—Sitall, glass—Kovar). For example, both the high reflectivity mirrors and the gas cell body in the embodiments herein can be made from fused silica or other glass material having a low thermal expansion coefficient, e.g., less than about $3 \times 10^{-6}$ m/m K. For embodiments where the same material is used for both the high reflectivity mirrors and the gas cell body, the temperature-induced stress can be rather small. If materials with a low thermal expansion coefficient are used for the cavity body and mirrors, the resonant cavity is much less sensitive to temperature variations.

The mirrors are typically high-reflectivity mirrors, each having a reflectivity of about 99% or greater (for certain wavelengths or wavelength ranges) on a surface facing an inside of the cavity body structure. In certain aspects, the reflectivity of the mirrors is greater than about 99.9%, or even 99.99%. Additional mounting components may be made of the same or different materials as the mirror elements.

Additional useful materials for the mirrors and/or the cavity body structure include Corning ULE® 7972 titania-silicate glass and Schott ZERODUR glass ceramic.

FIG. 1 (two separate views provided) shows an exemplary cavity enhanced optical spectroscopy (CEOS) system 10 according to one embodiment. CEOS system 10 includes a dual laser, single resonant cavity configuration for measurement of trace gases in air, according to an embodiment. CEOS system 10 is particularly useful for measuring multiple, e.g., 2 or 3 or more different, trace gases. Both the resonant cavity 20 and high reflectivity mirrors 25 are made of the same material (e.g., fused silica). The design using fused silica was successfully implemented in a prototype. In certain embodiments, at least one of the folding mirrors and/or at least one of the beam shaping optical elements can also be made from the same material (or with a material with similar thermal expansion characteristics) as the mirrors and cavity, e.g. fused silica.

CEOS system 10 includes a first light source 12 and a second light source 14, each of which emits continuous wave coherent light, such as continuous wave laser light, and an optical cavity 20. A detector system (including one or more photodetectors "PD") is provided and configured to measure absorption within the cavity, and hence an absorption coefficient, as well as other characteristics of incident and/or reflected light. In one embodiment, the detector system includes one or more detectors (PD) configured and arranged to measure optical signal emerging from one or more of the cavity mirrors. As shown, cavity 20 is a V-shaped cavity defined by cavity coupling mirror 25 and mirrors 26 and 27. One or more optical components (M) are configured and arranged to facilitate directing, and mode matching laser light from sources 12 and 14 to the optical cavity 20 via cavity coupling mirror 25. Optional beam splitting elements (BS) may be included. Cavity coupling mirror 25, in one embodiment, is arranged at an angle with respect to one or both incident source. A portion of incident light from each source enters cavity 20 via mirror 25. Depending on the frequency of incident light and the optical length of cavity 20 (e.g., optical length from mirror 27 to mirror 25 to mirror 26), light circulating in the cavity 20 may build up and resonate at one or a plurality of cavity modes (cavity resonances evenly separated in frequency; commonly known as the FSR or free spectral range of the cavity). A small portion of the intracavity light circulating in cavity 20 between mirror 27, 25 and 26, emerges or escapes via mirror 27 and also mirrors 26 and 25 as determined by their transmissivity. The light escaping mirror 25 is controlled by the various mirrors (M) and other optical elements to pass back to the sources 12 and 14, e.g., for optical feedback. In certain aspects, light returning to sources may pass through optional phase control and/or attenuation elements, which advantageously provides for phase and/or intensity control of the optical feedback provided to sources 12 and 14 from cavity 20. Examples of useful phase control and/or attenuation elements might include an electro-optic modulator that imposes a modulation on the phase of the light and an attenuation element such as a Faraday rotator.

An optional enclosure or housing (not shown) provides an air tight seal for components within the housing, such as cavity 20, laser sources 12 and 14 and the various optical mirror elements such as to allow control of the environment within the housing and hence also the cavity 20. Enclosed cavities are desirable for certain applications. The optional enclosure may be made of any sutable, structurally stable material, such as a metal or metal alloy, or a plastic material.

In certain embodiments, CEOS system 10 also includes a temperature sensor positioned and configured to measure a temperature of the gas within cavity 20 and a pressure sensor positioned and configured to measure a pressure of the gas within cavity 20. It should be appreciated that more than one temperature sensor may be used, and that more than one pressure sensor may be used. For example, a single temperature sensor may be used to determine a temperature internal to the cavity, or where gas is flowed through the cavity, for example, two temperature sensors may be used to determine a temperature at a gas inflow port and a gas exhaust port, from which a temperature of the gas in the cavity can be determined. In certain embodiments, the temperature and pressure of the gas in the cavity is controlled using a temperature control element and a pressure control element. Control of the ambient conditions, e.g., temperature and/or pressure, can be useful to help improve signal resolution and SNR.

In one specific embodiment, the approach of combining two laser beams into one may be used for a two laser three gas (e.g., CH4/CO2/H2O) optical feedback assisted cavity enhanced absorption spectroscopy analyzer. In certain aspects, two or more laser beams are combined first, and the combined beam is further coupled to an enhanced cavity. The optical feedback locks the laser light to the cavity modes. Various ways or means to combine two laser beams include using broadband beam splitters, using dichroic beam splitters or filters, and using polarization-dependent beam splitters.

In one specific embodiment, two DFB lasers operating at 1610 nm and 1653 nm may be used. A standard set of optics (an aspheric lens and a spherical lens) may be used to mode match the laser beams to the TEM00 mode of the V-shaped enhanced cavity. The vertex mirror 25 is a flat mirror and serves as a coupling mirror. Two end mirrors 26, 27 may be concave mirrors. The light transmitted through the cavity may be measured by the photodetector. The signal from the detector may be normalized on the incident light intensities measured by two detectors, one detector per laser. The lasers may operate in an interleaved mode.

Figure 2:
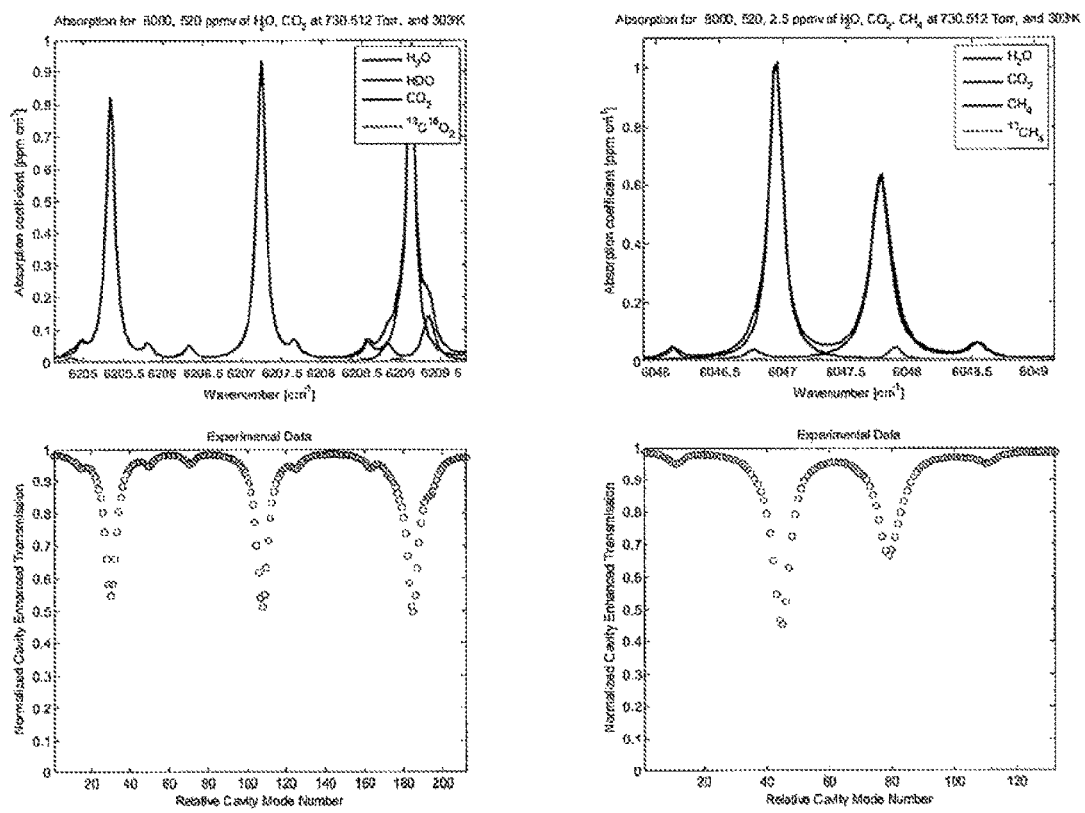
FIG. 2 shows experimentally measured spectra (bottom figures) of room air, and the top figures illustrate simulated spectra based on the HITRAN data base.

FIG. 2 shows experimentally measured spectra (bottom figures) of room air, and the top figures illustrate simulated spectra based on the HITRAN data base.

Figure 3:
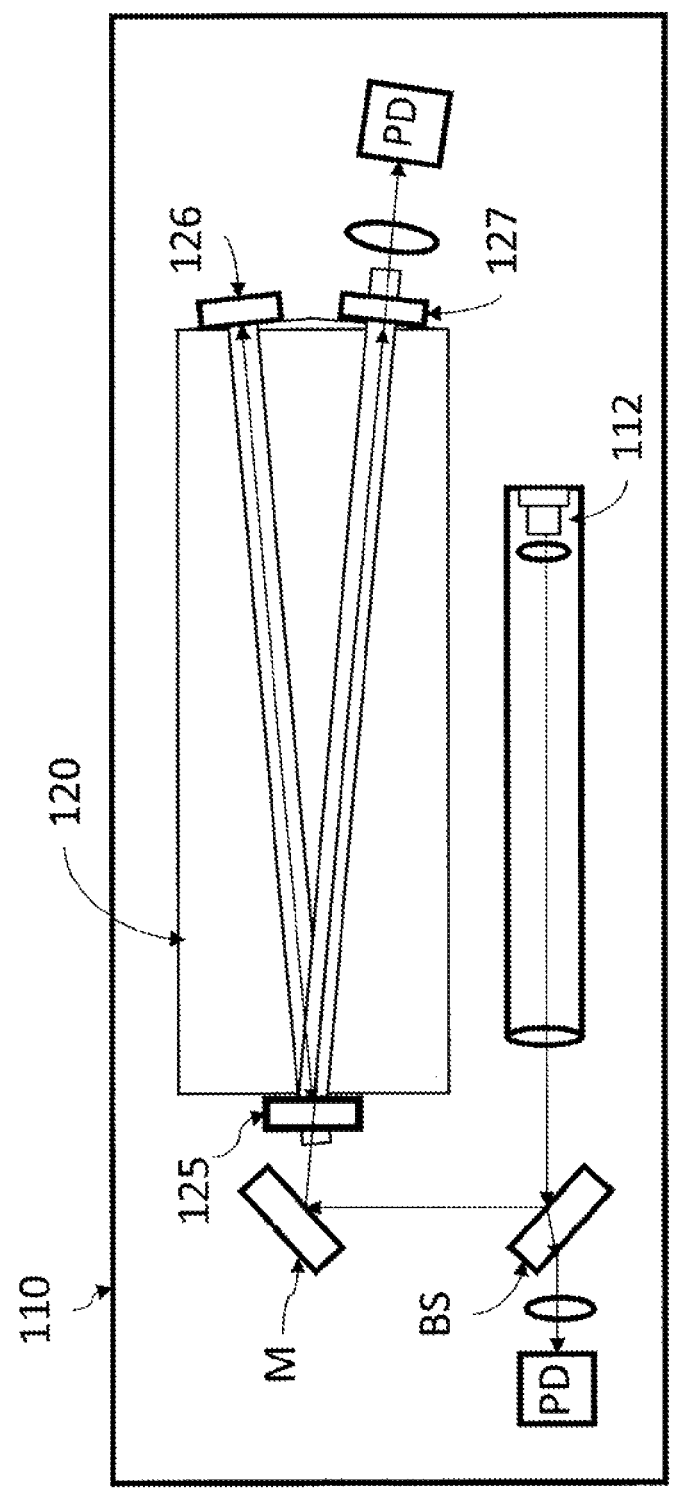
FIG. 3 shows a CEOS system including a single laser, single resonant cavity configuration for measurement of trace gases in air, according to an embodiment.

FIG. 3 shows a CEOS system 110 including a single laser, single resonant cavity configuration for measurement of trace gases in air, according to an embodiment. CEOS system 110 is particularly useful for measuring two trace gases. CEOS system 110 is similar to CEOS 10, but includes a single light source 112 that emits continuous wave coherent light, such as continuous wave laser light, and an optical cavity 120. A detector system (not shown) is provided and configured to measure absorption within the cavity, and hence an absorption coefficient, as well as other characteristics of incident and/or reflected light. In one embodiment, the detector system includes one or more detectors configured and arranged to measure optical signal emerging from one or more of the cavity mirrors. As shown, cavity 20 is a V-shaped cavity defined by cavity coupling mirror 125 and mirrors 126 and 127. One or more optical components, such as folding or directing mirrors (M) and/or lens elements, are configured and arranged to facilitate directing, and mode matching laser light from sources 112 to the optical cavity 120 via cavity coupling mirror 125. Optional beam splitting elements (BS) may be included. Depending on the frequency of incident light and the optical length of cavity 120 (e.g., optical length from mirror 127 to mirror 125 to mirror 126), light circulating in the cavity 120 may build up and resonate at one or a plurality of cavity modes (cavity resonances evenly separated in frequency; commonly known as the FSR or free spectral range of the cavity). A small portion of the intracavity light circulating in cavity 120 between mirror 127, 125 and 126, emerges or escapes via mirror 127 and also mirrors 126 and 125 as determined by their transmissivity. The light escaping mirror 125 is controlled by the various mirrors (M) and other optical elements to pass back to the source 112, e.g., for optical feedback. In certain aspects, light returning to sources may pass through optional phase control and/or attenuation elements, which advantageously provides for phase and/or intensity control of the optical feedback provided to source 112 from cavity 20. Examples of useful phase control and/or attenuation elements might include an electro-optic modulator that imposes a modulation on the phase of the light and an attenuation element such as a Faraday rotator.

Both the resonant cavity 120 and high reflectivity mirrors 125, 126 and 127 are made of the same material (e.g., fused silica). The design using fused silica was successfully implemented in a prototype. In certain embodiments, at least one of the folding mirrors and/or at least one of the beam shaping optical elements can also be made from the same material (or with a material with similar thermal expansion characteristics) as the mirrors and cavity, e.g. fused silica.

An optional enclosure or housing (not shown) provides an air tight seal for components within the housing, such as cavity 120, laser source 112 and the various optical elements such as to allow control of the environment within the housing and hence also the cavity 120. Enclosed cavities are desirable for certain applications.

In certain embodiments, system 110 also includes one or more temperature sensors positioned and configured to measure a temperature of the gas within cavity 120 and one or more pressure sensors positioned and configured to measure a pressure of the gas within cavity 120 as discussed above for FIG. 1. CEOS system 110 may also include temperature and/or pressure control elements as discussed above for FIG. 1.

In certain aspects, each source (e.g., 112 or 12 and 14) includes a laser or other coherent light source that is sensitive or responsive to optical feedback and that emits radiation at the desired wavelength(s) or desired wavelength range(s). One useful laser is a semiconductor diode laser that is sensitive to optical feedback from light impinging on the laser from the cavity coupling mirror (e.g., 25 or 125). Other laser sources might include diode lasers, quantum cascade lasers and solid state lasers. The reflectivities of the mirrors defining the cavity define the optical feedback intensity. U.S. Pat. No. 8,659,758, which is incorporated herein by reference in its entirety, discloses laser based cavity enhanced spectroscopy systems including mirror optimization techniques. It should be appreciated that the cavity coupling mirror (e.g., 25, 125) through which the laser light enters the cavity has a power reflectivity coefficient $R_1$ close to, but less than, unity such that the quantity $T=1-R_1$ is in the range from $10^{-1}$ to $10^{-5}$. The other cavity mirror(s) should have a power reflectivity $R_2$ equal to or lower than $R_1$. Such high reflective mirrors will certainly have some residual transmission, even though it may be as low as a few or several ppm.

In certain aspects, each source is capable of being frequency scanned, for example, a mean optical frequency of the laser is adjustable or tunable over a range of frequencies. This can be accomplished as is well known, such as, for example, by adjusting the current applied to a diode laser and/or adjusting a temperature of the laser medium. In certain aspects, the cavity (e.g., 20 or 120) is also capable of being frequency scanned, e.g., by changing or adjusting an optical length of the cavity, whereby an optical frequency of a cavity resonance peak is adjustable over a range of frequencies. Adjustment of the optical length of the cavity can include adjusting a relative position of one or more of the cavity mirrors (e.g., using a piezo element), and/or adjusting a pressure of the medium within the cavity. An intelligence module or control module, such as a computer system, processor, ASIC or other control circuitry, is provided to enable automated control of the source frequency tuning or scanning and/or cavity optical length adjustment.

In certain embodiments, the CEOS system (e.g., 10 or 110) is useful for detecting trace gases within a gas mixture present in the cavity. When the frequency of the incident light emitted by a source approaches the frequency of one of the cavity modes, the incident light entering the cavity begins to fill the cavity to that mode and may lock to that cavity mode. The optical intensity of the light circulating inside the resonance cavity reflects total cavity loss at the moment when the light frequency of incident light coincides with the cavity mode transmission peak. The total cavity loss is a sum of the cavity mirror losses and losses caused by absorption by the medium present in the cavity, e.g., absorption caused by absorbing analyte species present in the gaseous or liquid medium in the cavity. Examples of such species detectable by embodiments herein include $H_2O$, $N_2O$, NO, $NO_2$, $CO_2$, $CH_4$, various hydrogen, carbon, nitrogen and oxygen isotopes, and many others.

In various embodiments, the detector system is configured take measurements from which an absorption coefficient can be determined, e.g., based on measuring the intracavity optical power with and without an absorbing species present. For example, the power circulating inside the cavity ($P_{circ}$) is determined by the equation $P_{transm}=P_{circ}*T$, where T is the transmissivity of the mirror from which the light is escaping, and $P_{transm}$ is the power detected by the detector. A detector or detection element may be proximal to mirror element 27 or 127, for example. It should be appreciated that a detection element can additionally, or alternatively, be positioned to detect and measure the light escaping from mirror element 26 or 126 and/or mirror element 25 or 125 (e.g., reflected off of the backside of a beamsplitter (BS)). Also, a detection element could be configured and positioned internal to the cavity to measure the intracavity optical power. In certain embodiments, each detector element includes a photodetector, such as a photodiode, and associated electronics, for detecting light and outputting a signal representing the detected light. Examples of useful photodetectors might include silicon, InGaAs, Ge or GAP based photodetectors. Other useful detectors include CCDs, photomultipliers, etc. An intelligence module (e.g., a computer system, processor, ASIC or other control circuitry; not shown) receives the detector output signals and processes these signals to produce or generate a signal that characterizes the cavity loss based on the detection methodology used, e.g., PAS, free decay rate, phase shift, direct absorption, etc. For example, U.S. Pat. No. 8,659,759, which is incorporated herein by reference in its entirety, discloses laser based cavity enhanced spectroscopy systems including techniques for producing normalized signals that are a linear function of total cavity loss and that are not sensitive to laser-cavity coupling.

Additionally, as mentioned above, other detection methods can be used, for example, cavity ring-down spectroscopy methods, or cavity enhanced photo-acoustic spectroscopy (PAS) methods (see, e.g., U.S. Pat. No. 8,327,686, the contents of which are hereby incorporated by reference). Measurements made by the detector system are used to determine an absorption coefficient for any gas species or isotopes present in the cavity. For CRDS measurements, the ring-down decay time is measured and used to determine the absorption coefficient.

Figure 4:
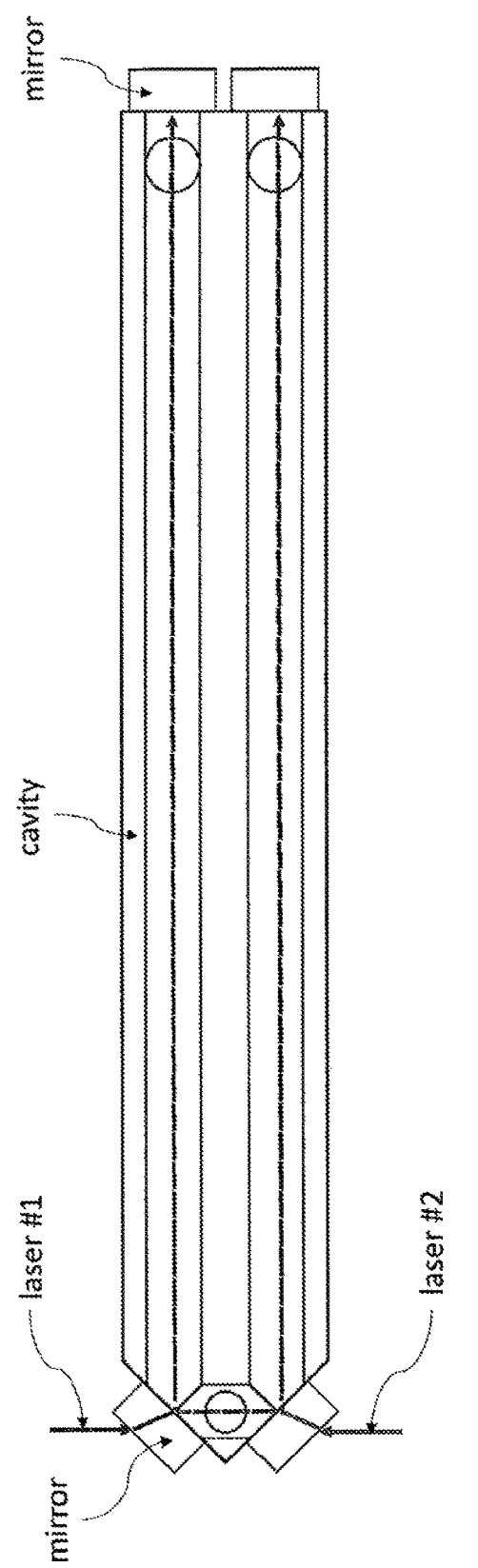
FIG. 4 (two separate views provided) shows apparatus configurations with 4 cavity mirrors according to different embodiments.
Figure 4:
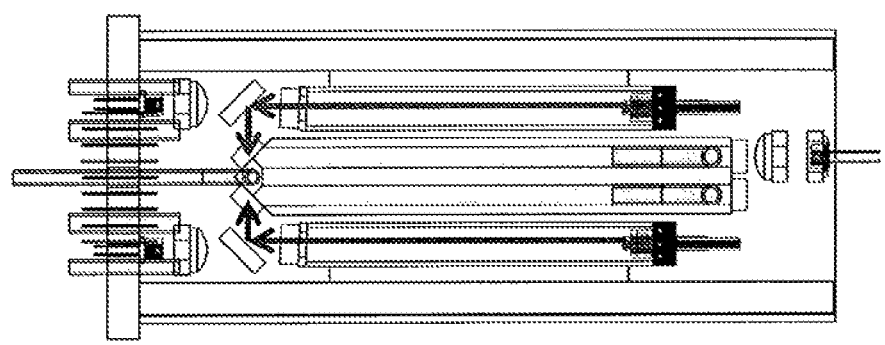
Figure 5:
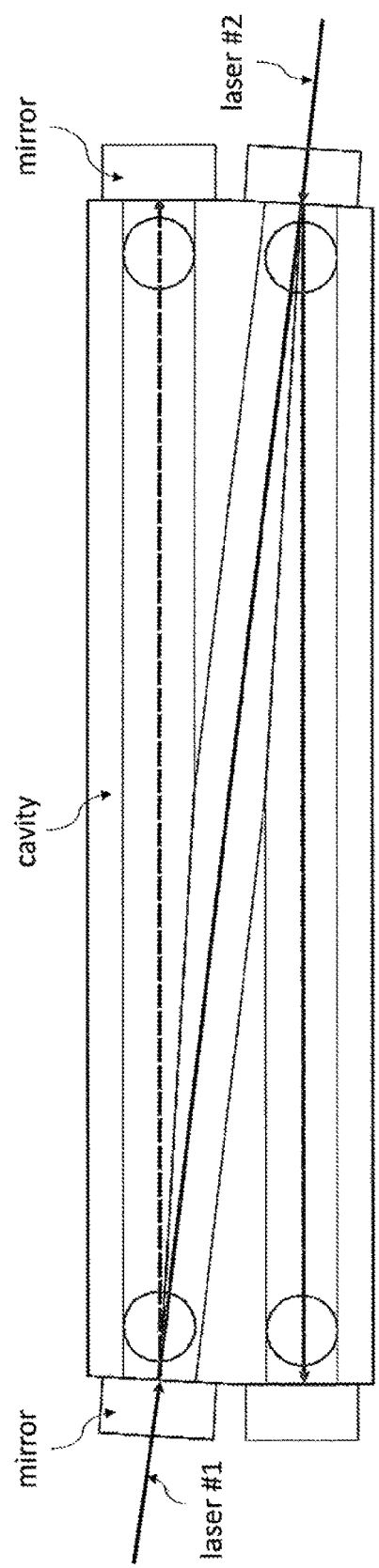
FIG. 5 (two separate views provided) shows apparatus configurations with 4 cavity mirrors according to different embodiments.
Figure 5:
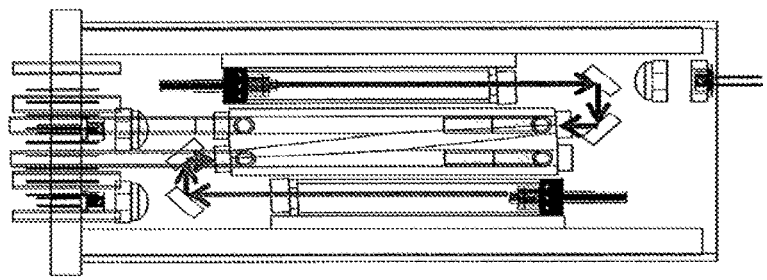

FIG. 4 (two separate views provided) and FIG. 5 (two separate views provided) show apparatus configurations with 4 mirrors according to different embodiments. The various component and operating principles of the CEOS systems and cavities in FIGS. 4 and 5 are similar to those described above with reference to FIGS. 1 and 2, however an additional mirror element is provided. For example, in FIG. 4, an additional mirror element is provided and a linear cavity with two arms is provided. Similarly, in FIG. 5, an additional mirror element is provided and a double-V-shaped cavity is provided. In FIGS. 4 and 5, both the resonant cavity and the high reflectivity mirrors may be made of the same material (e.g., fused silica), or of materials having the same or similar coefficient of thermal expansion. In certain embodiments, additional components of each CEOS system, such as at least one of the folding mirrors and/or at least one of the beam shaping optical elements, can also be made from the same material (or with a material with similar thermal expansion characteristics) as the mirrors and cavity, e.g. fused silica.

Figure 6:
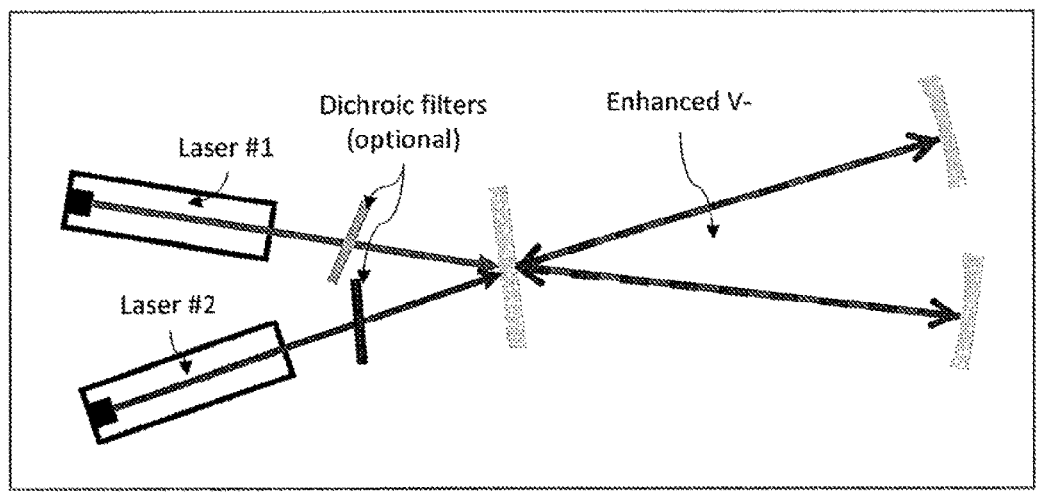
FIG. 6 shows an embodiment of a cavity having three mirrors and only one mirror is used to couple two or more lasers.

FIG. 6 shows an embodiment where the cavity has three mirrors and only one mirror is used to couple two or more lasers. In this embodiment, two (or more) dichroic filters are used to reduce the laser interference effect. Each filter transmits only radiation of the corresponding laser. If two lasers are coupled into two orthogonal polarized cavity modes, polarizers can be used instead of dichroic filters.

Another embodiment includes using cavities with more than one coupling mirror. Two exemplary configurations are shown above in FIGS. 4 and 5, where two different mirrors are used to couple laser light from two different laser sources: FIG. 4 shows a Π-shaped cavity, and FIG. 5 shows an N-shaped cavity.

Figure 7:
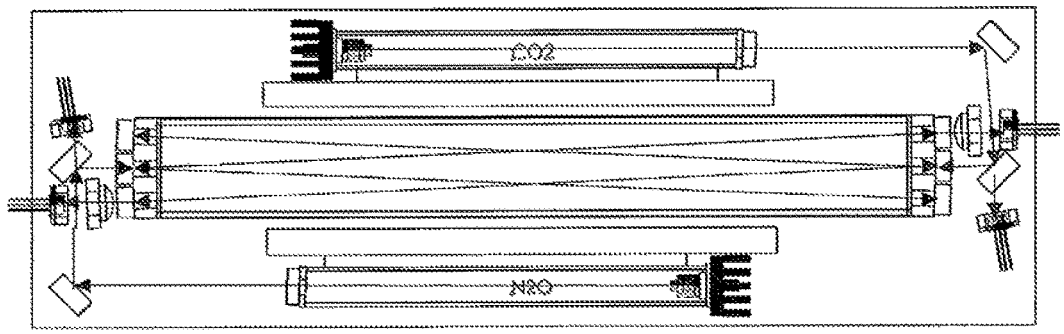
FIG. 7 shows two optical enhanced cavities sharing the same cavity volume according to an embodiment.

There are situations when two or more optical enhanced cavities are required to measure gases having analytical absorption lines in very different spectral regions (e.g., carbon dioxide lines are at 1.61 μm, while nitrous oxide lines are at 2.11 μm). So, it would almost be nearly impossible or it would be too expensive to have the cavity mirrors suitable for both spectral regions. In that case, according to an embodiment, two optical cavities share the same gas volume, as shown in FIG. 7. Red arrows represent the laser beam emitted by a laser to measure $N_2O$ concentration, while blue arrows represent the laser beam emitted by a laser to measure $CO_2$ concentration.

Figure 8:
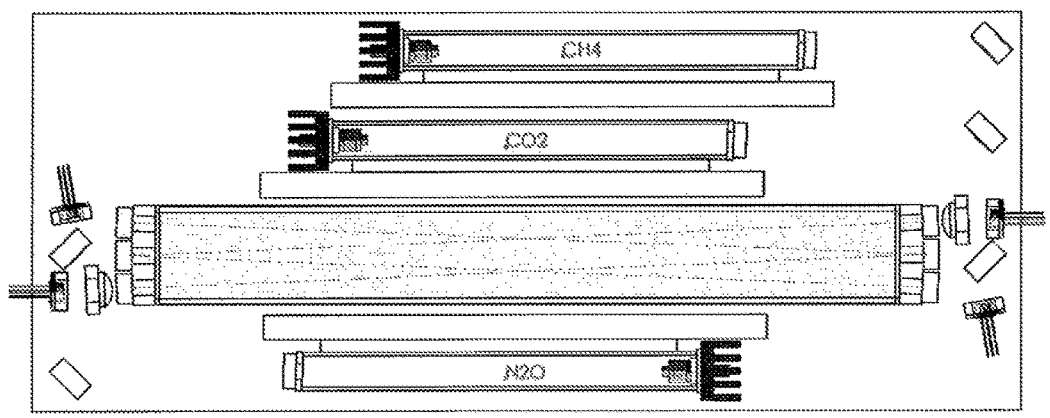
FIG. 8 shows an embodiment of an analyzer using three different lasers.

More complex configurations are also possible. FIG. 8 shows an embodiment of an analyzer using three different lasers. Two lasers (e.g., emitting at absorption lines for $CO_2$ & $CH_4$) are coupled to the same enhanced cavity by using a beam splitter. The third (e.g., $N_2O$) laser is coupled into the second enhanced cavity. Both cavities share the tested gas volume.

Figure 9:
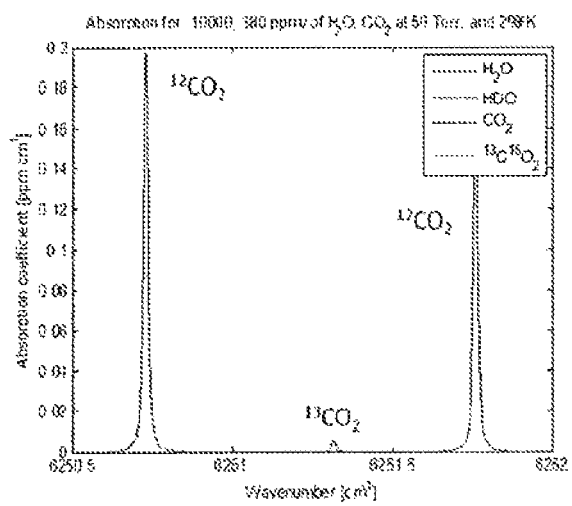
FIGS. 9-11 show a typical situation when absorption spectra in three different spectral regions are measured for the determination of $CO_2$, $CH_4$, water concentrations, and $^{13}CO_2/^{12}CO_2$, $^{13}CH_4/^{12}CH_4$ ratios.
Figure 10:
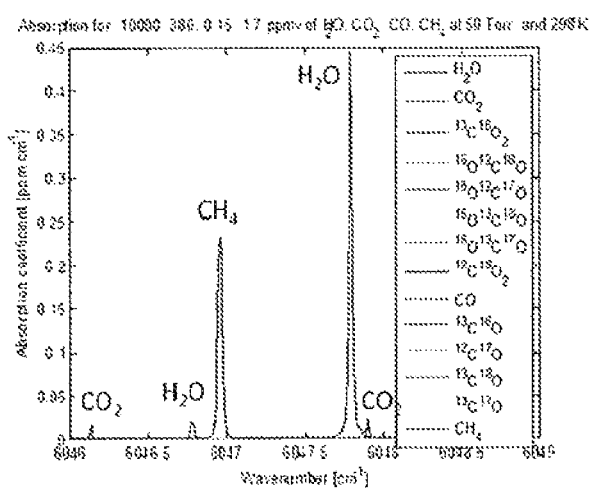
Figure 11:
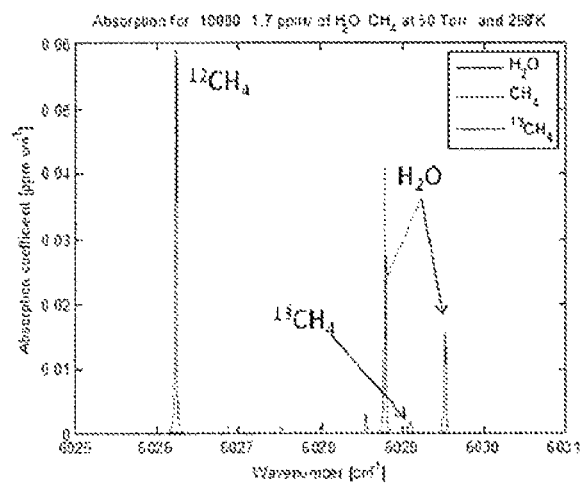

FIGS. 9-11 show a typical situation when absorption spectra in three different spectral regions are measured for the determination of $CO_2$, $CH_4$, water concentrations, and $^{13}CO_2/^{12}CO_2$, $^{13}CH_4/^{12}CH_4$ ratios. In general, a resonant optical cavity can be independently locked to any absorption line in each scanned spectral region. However, it might require tuning of the cavity modes for each scan. In this case, the locking accuracy or the accuracy of the frequency determination of the cavity modes will vary for each scan, because the locking accuracy is defined by the derivatives of the absorption profiles at frequencies of the cavity modes and noise in the cavity loss measurements. The last quantity is almost constant.

Figure 12:
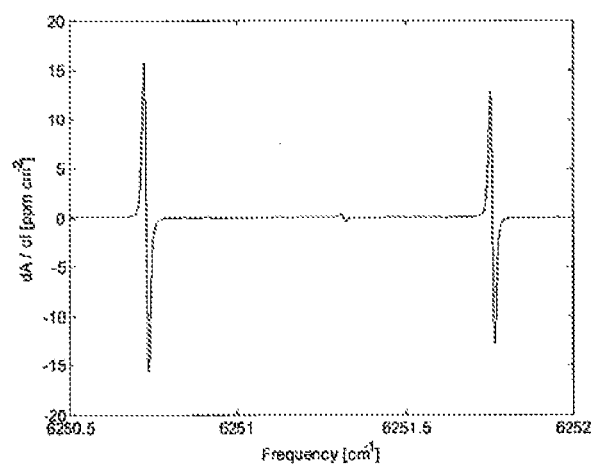
FIGS. 12-14 show derivatives of the absorption spectra of FIGS. 9-11, respectively.
Figure 13:
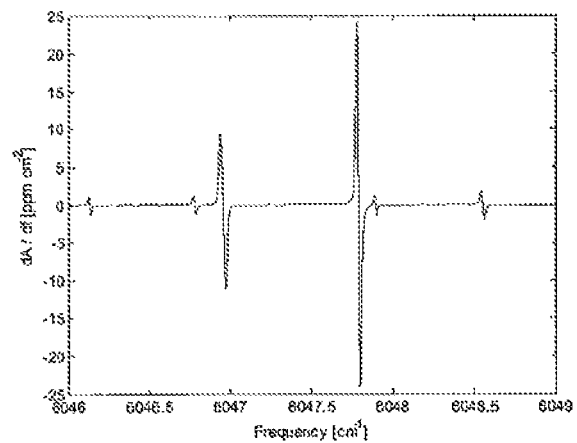
Figure 14:
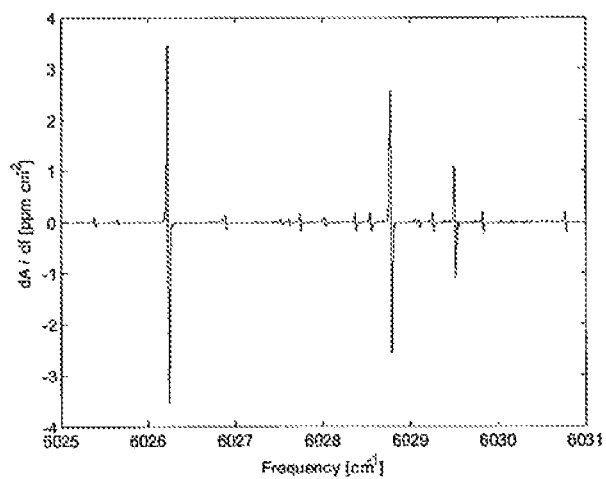

FIGS. 12-14 show derivatives of the absorption spectra of FIGS. 9-11, respectively. One can see that the biggest value for derivatives of the absorption spectra at 50 Torr has the water line at 6047.79 $cm^{-1}$. However, a water line is probably not the best choice as a reference line for the cavity grid, because the humidity of the air might vary significantly. Calibrated gases used for instrument calibrations have a very small amount of water vapor.

One of the candidates for a reference line can be the carbon dioxide line at 6250.73 $cm^{-1}$. The carbon dioxide concentration in the air is usually higher than 300 ppm. So, this line might be used as a reference line for a fixed cavity instrument, which measures absorption in all mentioned above spectral regions. A fixed cavity instrument is defined as an instrument with a cavity with fixed length during laser scans. However, the cavity length can be changed (tuned) between scans by changing the physical length of the cavity, or by changing the optical length of the cavity without changing its physical length. The last one can be done by changing the gas pressure.

Reference is also made to U.S. Pat. Nos. 8,659,758, 8,659,759, 8,885,167 and 8,665,442, which are each hereby incorporated by reference for all purposes, for gas analyzer systems and applications for which the present embodiments are useful.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for detecting two or more analyte species present in a gaseous or liquid medium, the system comprising:

a resonant optical cavity containing said medium and having at least six cavity mirrors, two of which are cavity coupling mirrors, the cavity having a plurality of optical resonance cavity modes;

a first laser that emits continuous wave laser light, wherein the first laser is capable of being scanned whereby a mean optical frequency of the first laser is adjustable over a range of frequencies, and wherein the first laser is responsive to optical feedback light emerging from the cavity;

first mode matching optics including one or more optical components configured to couple the first laser light to the cavity via a first cavity coupling mirror at an angle non perpendicular to a mirror reflective surface of the first cavity coupling mirror, wherein the first laser light travels along a first path within the resonant optical cavity;

a second laser that emits continuous wave laser light, wherein the second laser is capable of being scanned whereby a mean optical frequency of the second laser is adjustable over a range of frequencies, and wherein the second laser is responsive to optical feedback light emerging from the cavity;

second mode matching optics including one or more optical components configured to couple the second laser light to the cavity via a second cavity coupling mirror at an angle non perpendicular to a mirror reflective surface of the second cavity coupling mirror, wherein the second laser light travels along a second path within the resonant optical cavity, the second path being different than the first path; and at least one detector configured to measure an intensity of the intra-cavity optical power of light circulating in the cavity along the first path or the second path and to generate a signal representing the intra-cavity optical power of light circulating in the cavity.

2. The system of claim 1, wherein the transmissivity of the first cavity coupling mirror is selected such that the intensity of the optical feedback light impinging on the first laser is below a threshold intensity value so as to ensure that a frequency hold interval range of the optical frequency of the first laser is smaller than a free spectral range of the cavity.

3. The system of claim 1, wherein the transmissivity of the second cavity coupling mirror is selected such that the intensity of the optical feedback light impinging on the second laser is below a threshold intensity value so as to ensure that a frequency hold interval range of the optical frequency of the second laser is smaller than the free spectral range of the cavity.

4. The system of claim 1, wherein the at least one detector includes a first detector configured to measure an intensity of the intra-cavity optical power of light circulating in the cavity along the first path, and a second detector configured to measure an intensity of the intra-cavity optical power of light circulating in the cavity along the second path.

5. A system for detecting one or more analyte species present in a gaseous or liquid medium, the system comprising:

a resonant optical cavity containing said medium and having at least two cavity mirrors, one or more of which are cavity coupling mirrors, the cavity having a plurality of optical resonance cavity modes;

a first laser that emits continuous wave laser light, wherein the first laser is capable of being scanned whereby a mean optical frequency of the first laser is adjustable over a first range of frequencies;

mode matching optics including one or more optical components configured to couple the first laser light to the cavity via one of the cavity coupling mirrors;

a second laser that emits continuous wave laser light, wherein the second laser is capable of being scanned whereby a mean optical frequency of the second laser is adjustable over a second range of frequencies non identical to the first range of frequencies;

mode matching optics including one or more optical components configured to couple the second laser light to the cavity via one of the cavity coupling mirrors; and at least one detector configured to measure an intensity of the intra-cavity optical power of light circulating in the cavity and to generate a signal representing the intra-cavity optical power of light circulating in the cavity wherein the cavity modes are locked to one or more spectral absorption lines of the one or more analyte species presented in the first range of frequencies.

6. A system for detecting two or more analyte species present in a gaseous or liquid medium, the system comprising:

a resonant optical cavity containing said medium and having at least two cavity mirrors, one or more of which are cavity coupling mirrors, the cavity having a plurality of optical resonance cavity modes;

a first laser that emits continuous wave laser light, wherein the first laser is capable of being scanned whereby a mean optical frequency of the first laser is adjustable over a first range of frequencies;

mode matching optics including one or more optical components configured to couple the first laser light to the cavity via one of the cavity coupling mirrors;

a second laser that emits continuous wave laser light, wherein the second laser is capable of being scanned whereby a mean optical frequency of the second laser is adjustable over a second range of frequencies non identical to the first range of frequencies;

mode matching optics including one or more optical components configured to couple the second laser light to the cavity via one of the cavity coupling mirrors;

at least one detector configured to measure an intensity of the intra-cavity optical power of light circulating in the cavity and to generate a signal representing the intra-cavity optical power of light circulating in the cavity; and an intelligence module including control circuitry configured to assign frequencies for a cavity mode grid based on spectral absorption lines of the analyte species presented in the first range of frequencies.

7. The system of claim 6, wherein the control circuitry includes one of a computer system, a processor or an ASIC.

* * * * *